United States Patent
Thundat et al.

(10) Patent No.: US 7,090,757 B2
(45) Date of Patent: Aug. 15, 2006

(54) PHOTOELECTROCHEMICAL MOLECULAR COMB

(75) Inventors: Thomas G. Thundat, Knoxville, TN (US); Thomas L. Ferrell, Knoxville, TN (US); Gilbert M. Brown, Knoxville, TN (US)

(73) Assignee: UT-Battelle LLC, Oak Ridge, TN (US)

( * ) Notice: Subject to any disclaimer, the term of this patent is extended or adjusted under 35 U.S.C. 154(b) by 135 days.

(21) Appl. No.: 10/077,633

(22) Filed: Feb. 15, 2002

(65) Prior Publication Data

US 2003/0157698 A1 Aug. 21, 2003

(51) Int. Cl.
*G01N 27/447* (2006.01)
*G01N 27/453* (2006.01)

(52) U.S. Cl. .................... 204/450; 204/600

(58) Field of Classification Search ............... 204/450, 204/554, 600, 606, 608, 660, 663, 672, 456, 204/457; 136/255, 291
See application file for complete search history.

(56) References Cited

U.S. PATENT DOCUMENTS

| | | | | |
|---|---|---|---|---|
| 5,151,741 A | * | 9/1992 | Kakutani et al. | 399/131 |
| 5,500,188 A | * | 3/1996 | Hafeman et al. | 204/403.01 |
| 5,985,568 A | * | 11/1999 | Krihak et al. | 435/6 |
| 6,203,985 B1 | * | 3/2001 | Jiang et al. | 435/6 |
| 6,706,473 B1 | * | 3/2004 | Edman et al. | 435/6 |
| 6,730,208 B1 | * | 5/2004 | Bruel | 205/91 |

FOREIGN PATENT DOCUMENTS

| | | |
|---|---|---|
| WO | WO 98/57157 | 12/1998 |
| WO | WO 00/13784 | 3/2000 |

OTHER PUBLICATIONS

Gurtner et al., "Photoelectrophoretic Transport and Hybridization of DNA Oligonucleotides on Unpatterned Silicon Substrates", Journal of the American Chemical Society vol. 122, No. 36 (Sep. 13, 2000), pp. 8589-8594.*

(Continued)

*Primary Examiner*—Alex Noguerola
(74) *Attorney, Agent, or Firm*—McDonnell Boehnen Hullbert & Berghoff LLP

(57) ABSTRACT

A method and apparatus for separating molecules. The apparatus includes a substrate having a surface. A film in contact with the surface defines a substrate/film interface. An electrode electrically connected to the film applies a voltage potential between the electrode and the substrate to form a depletion region in the substrate at the substrate/film interface. A photon energy source having an energy level greater than the potential is directed at the depletion region to form electron-hole pairs in the depletion region. At least one of the electron-hole pairs is separated by the potential into an independent electron and an independent hole having opposite charges and move in opposing directions. One of the electron and hole reach the substrate/film interface to create a photopotential in the film causing charged molecules in the film to move in response to the localized photovoltage.

31 Claims, 2 Drawing Sheets

OTHER PUBLICATIONS

Ozkan et al., "Heterogeneous Integration through Electrokinetic Migration", IEEE Engineering in Medicine and Biology (Nov./Dec. 2001), pp. 144-151.*

C. Gurtner et al., "Photoelectropheretic Transport and Hybridization of DNA Oligonucleotides on Unpatterned Silicon Substrates", *Journal of the American Chemical Society*, vol. 122, No. 36 (2000), pp. 8589-8594.

Inoue S et al, "Chemical-Imaging Sensor Using Enzyme", Sensors and Actuators B, Elsevier Sequoia S.A., vol. B32, No. 1, Apr. 01, 1996, pp. 23-26, XP000636382.

Brown G N et al, "Development and Characterization of a Titanium Dioxide-Based Semiconductor Photoelectrochemical Detector" Analytical Chemistry, American Chemical Society, Columbus, vol. 64, No. 4, Feb. 15, 1992, pp. 427-434, XP000261109.

Owicki J C et al, "The Light-Addressable Potentiometric Sensor: Principles and Biological Applications", Annual review of Biophysics and Biomolecular Structure, Palo Alto, CA, vol. 23, 1994, pp. 87-113, XP002073025.

* cited by examiner

PHOTOELECTROCHEMICAL MOLECULAR COMB

STATEMENT REGARDING FEDERALLY SPONSORED RESEARCH

This invention was made with government support under contract DE-AC05-00OR22725, awarded by the United States Department of Energy to UT-Battelle, LLC, and the United States Government has certain rights in this invention.

CROSS REFERENCES TO RELATED APPLICATIONS

Not Applicable

BACKGROUND OF THE INVENTION

The present invention relates to separating charged molecules, such as DNA, proteins, polypeptides, and other molecules or charged particles using a photoelectrochemical method.

Analysis of a sample of biological origin frequently requires the separation of mixtures, and biomolecules, such as nucleic acids, proteins, and polypeptides, which often have limited sample size. Electrophoresis, in which charged molecules move in a liquid under the influence of an electric field, has long been the method of choice for separating many classes of biomolecules. This method takes advantage of differing migration velocities, $v_{ep}$, of different molecules.

Migration velocity, $v_{ep}$, the distance the molecule or particle moves (L) per unit time (t), is the product of the electrophoretic mobility, $\mu_{ep}$, times the electric field strength E (units of volts/cm).

$$v_{ep} = \mu_{ep} \times E \quad \mu_{ep} = q/6\pi\eta R$$

where q is the charge on the particle and η is the viscosity of the medium. The velocity is, thus, directly proportional to the charge on the particle and the field strength and inversely proportional to the size of the particle and the viscosity of the medium. For relatively large particles or biomolecules, the charge increases as the size of the molecule increases, and the charge to mass (or radius) ratio becomes nearly constant. Under these circumstances if the electrophoresis is carried out in the presence of a gel composed of agrose or crosslinked polyacrylamide, the gel structure creates a molecular sieving effect that allows the molecules or particles to be separated on the basis of size.

Capillary gel electrophoresis is typically carried out in 50 μm diameter capillaries that are 10 cm to 1 m long with a field strength that is generally in the range of 100 V/cm to 500 V/cm, and requires a high-applied voltage greater than 1 KV. Heat generation is directly proportional to the square of the applied voltage, and the voltages required to achieve separation in capillary electrophoresis may cause degradation of sensitive samples.

Transport of biomolecules has been demonstrated when applying voltages less than 1 KV. Semiconductors such as Si, Ge, GaAs, $TiO_2$, CdS, and ZnO in contact with a liquid exhibit a change in surface charge upon irradiation with light of an appropriate wavelength when electronic bands of the semiconductors are bent. These reactions occur initially by the absorption of photons of energies greater than the corresponding semiconductor band gap to form conduction band electron-valence band hole pairs. This phenomenon has been shown to be advantageous for the photoelectrophoretic transport of biomolecules, but prior to the present disclosure has not been used for separating biomolecules.

Band bending can be achieved by suitably polarizing the semiconductor with respect to the liquid with a power supply. The back contact to the semiconductor electrode is Ohmic in character while the semiconductor-liquid interface acts as a Schottky barrier. Therefore, most of the applied voltage is dropped at the semiconductor-liquid interface creating a space charge (depletion or accumulation) layer in the semiconductor. The formation of depletion or accumulation layer depends on the bias and the type of semiconductor. The nature of band bending can be changed from depletion to accumulation by changing the sign of the applied potential with respect to flat band potential of the semiconductor-liquid interface.

Irradiation of the semiconductor-liquid interface with photons of appropriate energy produces electron-hole pairs in the depletion or accumulation layer. The field in the depletion or accumulation layer separates the electron-hole pairs. For example, for a n-type semiconductor, the bands are bent down for a depletion layer, and therefore the electrons come to the semiconductor-liquid interface during illumination. In the case of an accumulation layer irradiation causes the holes to accumulate at the solid-liquid interface. The presence of a charge on the semiconductor can be used for attracting charged biomolecules.

An experiment conducted by Gurtner et al demonstrated that DNA oligonucleotides could be photoeletrophoretically transported to a stabilized semiconductor surface coated with a streptavidin-agarose permeation layer (C. Gurtner, C. Edman, R. Formosa, M. Heller, Photoelectrophoretic Transport and Hybridization of DNA Oligonucleotides on Unpatterned Silicon Substrates, *Journal of the American Chemical Society*, vol. 122, no. 36, (2000) pp 8589–8594.). In this experiment, micro-illumination of the surface generated photoelectrochemical currents that were used to electrophoretically transport biointylated DNA capture strands to arbitrarily selected locations for attachment. These experiments demonstrate that a photogenerated potential is sufficient to cause movement in biointylated DNA capture strands.

A subject of a considerable amount of research in recent years has been microscale fluid handling systems that perform fast, automated, high-resolution sample preparation, reaction, and separation. Currently, this is being accomplished through advances in microfluidics. The idea is that once the manipulation of fluids can be mastered on the microscale, key experiments for biomolecule separation and analysis can be integrated and automated—all on a mass-produced chip. In microfluidic-based devices, DNA, proteins, and other molecules are transported, manipulated, and separated through miniature channels embedded into the chip. Detection systems can also be integrated into the chip or affixed externally as a separate component for seamless, automated and highly sensitive detection.

SUMMARY OF THE INVENTION

The present invention provides a microscale method and apparatus for performing chemical separation of biomolecules such as DNA, proteins, polypeptides, and peptides on a chip using photoelectrochemistry. Advantageously, the present invention provides a method of separation and analysis that requires neither miniature channels nor capillary tubes for the separation and analysis of the same class of biomolecules.

The photoelectrochemical molecular comb technology disclosed herein utilizes an electrokinetic phenomenon and semiconductor photoelectrochemistry to create a spatially confined electric field on a microchip which is used to transport and separate biomolecules without the use of channels. This innovative technology has the potential to provide substantial cost and performance advantages for users, including minimizing the amount of the sample required, minimizing the time of a process, increasing analysis flexibility and complexity, and improving separation resolution.

A general objective of the present invention is to provide a relatively low-voltage apparatus and method for separating molecules. This objective is accomplished by creating a localized photovoltage that moves analyte molecules, as opposed to creating a static field gradient requiring a higher voltage Another objective of the present invention is to provide an inexpensive method and apparatus for separating molecules, such as DNA, proteins, and other molecules using electrochemistry. This objective is accomplished by providing an apparatus and method that can separate molecules using an applied voltage of preferably less than 10V.

This and still other objectives and advantages of the present invention will be apparent from the description which follows. In the detailed description below, preferred embodiments of the invention are described in reference to the accompanying drawings. These embodiments do not represent the full scope of the invention. Rather the invention may be employed in other embodiments. Reference should therefore be made to the claims herein for interpreting the breadth of the invention.

DETAILED DESCRIPTION OF THE INVENTION

Figure 1:
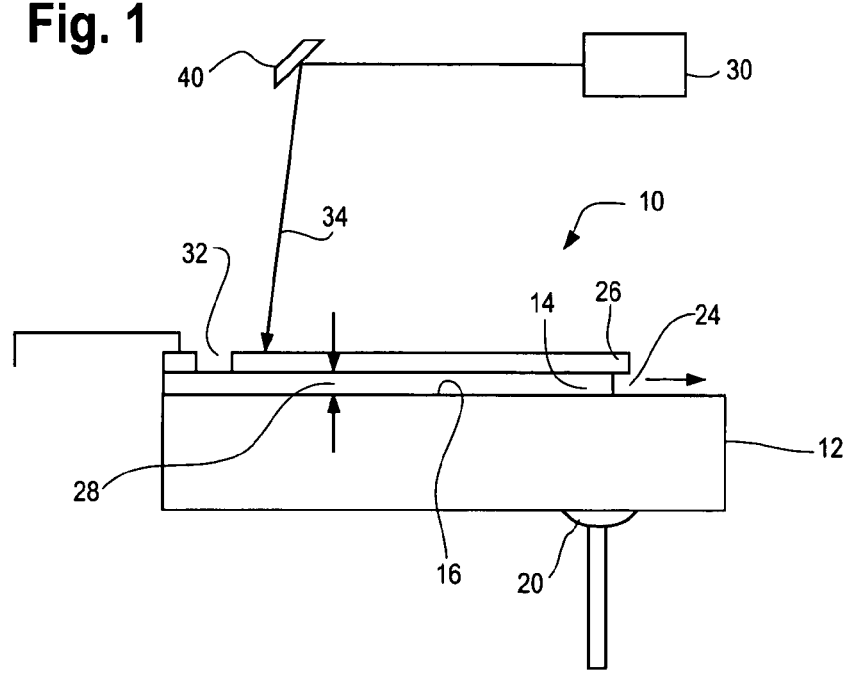
FIG. 1 is a side view of an apparatus incorporating the present invention.

The novel method utilizes an electrolyte buffer sandwiched between a semiconductor substrate and a transparent counter electrode to complete an electrical circuit between the semiconductor and the transparent counter electrode. When the semiconductor is in contact with an electrolyte solution, a double layer of charge (dipole layer) is well-known to be established at the interface.

Proper biasing of the semiconductor-liquid interface results in the subsequent creation of a charge-depletion layer in the semiconductor. The biomolecule of interest is localized within a given spot area in the buffer between the semiconducting and conducting (but transparent) electrodes. Irradiation of the spot containing the biomolecules with a focused beam of photons of energy greater than the band gap of the semiconductor generates new charge carriers in the charge-depletion layer. The thereby-separated charge carriers reach the interface of the semiconductor and electrolyte and create a localized photovoltage.

The charged biomolecules move in response to the electric field provided by this low voltage. If the focused beam is scanned to an adjacent spot on the semiconductor, the molecules move along with the light beam because they are attracted to this newly irradiated and spatially distinct spot by the above described change in the electrokinetic potential. If the buffer solution also contains a molecular sieving agent, this movement of molecules that results from the photoinduced potential changes allows different molecules to be separated by size, a process completely analogous to that which occurs in gel electrophoresis. By properly adjusting the scan speed, different molecules can be separated with extreme precision. This technique allows for separation in multiple directions, utilizing any or all of the properties of size, mass, and ionization-potential of the biomolecules that are intended for high-resolution separation on a microchip. This sieving action can be accomplished by artificially patterning the surface to provide a resistance to the movement of the charged particles.

The light source is focused to produce a point of intense light so that the electrons arriving at the interface are highly localized. Preferably, the light source is pulsed so that no saturation phenomenon occurs. The magnitude of the photovoltage induced is proportional to the light intensity and the extent of the band bending. The latter can be controlled by adjusting the biasing voltage.

The direction of the photoelectrophoresis action is between the irradiated spot on the semiconductor electrode and the electrode. Preferably, a reversing potential is applied between the two electrodes during the "light-off" cycle of the repetitive pulses. This moves the molecules in the opposite direction so they can again be attracted to the semiconductor when the focused laser beam is moved to an adjacent spot. When a line of instantaneous photopotential is created between the substrate and counter electrode, the analyte molecules move towards the counter electrode. Since the light beam is scanned, the molecules end up being transported after multiple steps in a direction parallel to the two electrodes, i.e. the semiconductor substrate and counter electrode. As a result, scanning the light beam makes the molecules migrate in the same direction as the direction of scan. Interaction of the biomolecules of interest with the gel matrix makes it possible to separate the molecules of different mobilities or of different sizes.

Referring to FIGS. 1–4, an apparatus 10 for separating molecules, such as DNA, proteins, polypeptides, and the like, includes a substrate 12 covered by a film 14 to define a substrate/film interface 16. A localized potential induced in the film 14 forces charged molecules (not shown) in the film 14 to move in a specific direction toward either an electrode 26 or the substrate 12.

The substrate 12 is a semiconductor in which a charge-depletion region 18 can be formed at the substrate surface 22 by applying a voltage potential across the substrate/film interface 16. The substrate 12 can be formed from p-type or n-type materials known in the art, such as Si, Ge, GaAs, CdS, ZnO, $TiO_2$, and the like. Preferably, the substrate 12 is cleaned prior to applying the film 14 to ensure that the voltage potential can be applied across the substrate/film interface 16. For example, oxides on a Ge substrate can be cathodically reduced or removed using a mild etching solution Preferably, an ohmic contact 20 is electrically connected to the substrate 12 in order to maintain the integrity of the voltage potential applied across the substrate/film interface 16. An ohmic contact 20 is a metal-semiconductor contact with a linear current-voltage characteristic and low resistance, and is well known in the art.

The film 14 is a thin layer of an electrically conductive fluid, such as crosslinked polyacrylamide, agarose, and the like, containing an electrolyte and buffer substances which is brought into contact with the cleaned surface 22 of the substrate 12 to form the substrate/film interface 16. The film 14 contains the molecules being separated, and preferably resists movement of the molecules to provide consistent separation of the molecules of interest.

The resistive properties of the film 14 can be enhanced by providing the film 14 in the form of a gel, or by providing the substrate 12 with a roughened or artificially patterned surface 22 at the substrate/film interface 16. In addition, the resistive property of the film 14 can be enhanced by providing a thin layer of buffer solution, such as a phosphate buffer, at the substrate/film interface 16.

An electrode 26 is placed in contact with the film 14 to apply the voltage potential across the substrate/film interface 16. Preferably, the electrode 26 is optically transmissive, such as a transparent conductor formed from indium tin oxide (ITO). The electrode 26 can be coated, such as with silane, such that the analyte molecules do not adhere to the electrode 26. Although an electrode formed from ITO is disclosed, other transparent materials can be used, such as glass or quartz with a thin, transmissive layer of a conductive material, such as gold or platinum deposited on the side of the electrode 26 that is in contact with the liquid, without departing from the scope of the invention.

Figure 2:
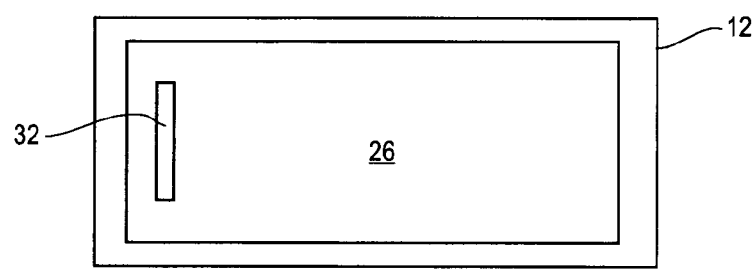
FIG. 2 is a top view of the apparatus of FIG. 1.
Figure 3:
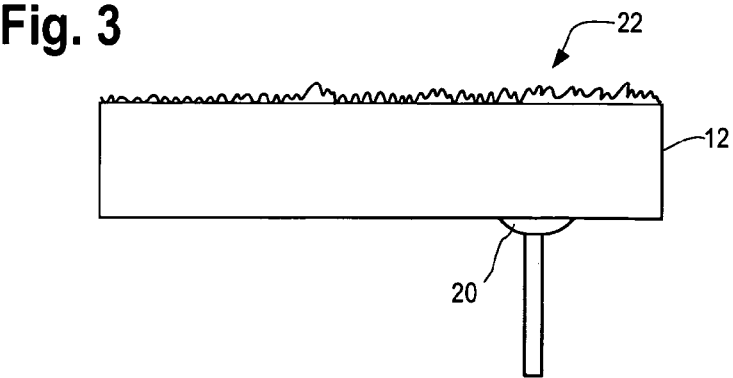
FIG. 3 is a detailed view of the substrate of FIG. 1.

In the embodiment disclosed in FIGS. 1 and 2, the electrode 26 is spaced from the substrate 12, and defines a gap 28 between the electrode 26 and substrate 12 containing the film 14. Preferably, the gap is less than a few millimeters, such as three millimeters, and is sufficiently large to allow analyte molecules to move within the film. The gap, however, can be more or less than a few millimeters without departing from the scope of the present invention.

An aperture 32 formed through the electrode 26 provides an inlet for filling the gap 28 with the film 14 and the adding molecules for separation. The surface tension of the film 14 maintains the film 14 between the substrate 12 and electrode 26 until an excess amount of film 14 is deposited through the inlet. Sidewalls (not shown) can be provided which direct any excess film to an outlet 24.

Figure 4:
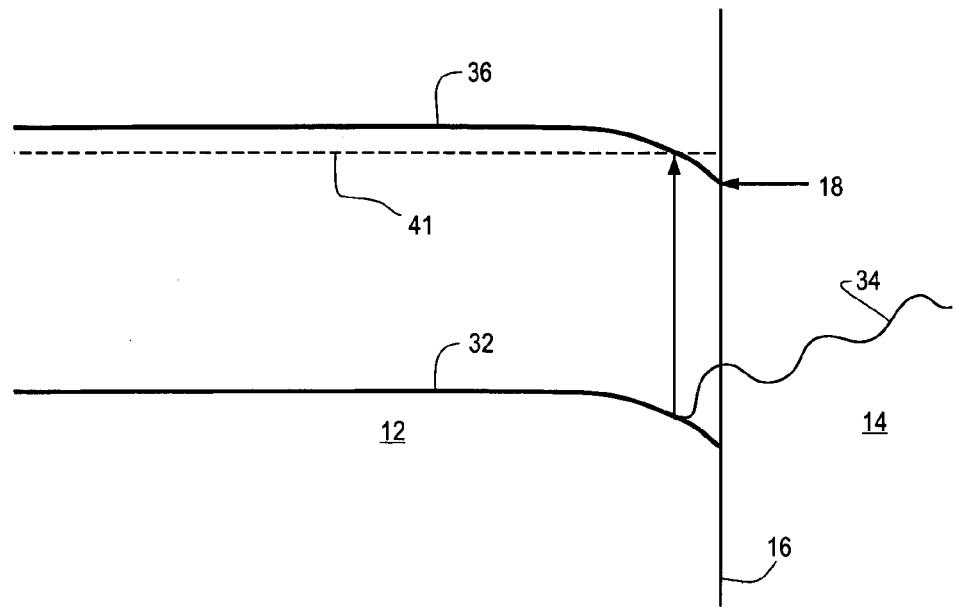
FIG. 4 is an energy band diagram at the substrate/film interface during the operation of the apparatus of FIG. 1.

As shown in FIG. 4, applying the voltage potential across the substrate/film interface 16 bends the conduction and valence bands 36, 38 in the substrate 12. Bending the conduction band 36 below the Fermi level 41 for the substrate 12 creates the depletion region 18 in the substrate 12 at the substrate/film interface 16. The depletion region 18 can provide a source of electrons or holes to create a photopotential in the film 14, as discussed below.

Figure 5:
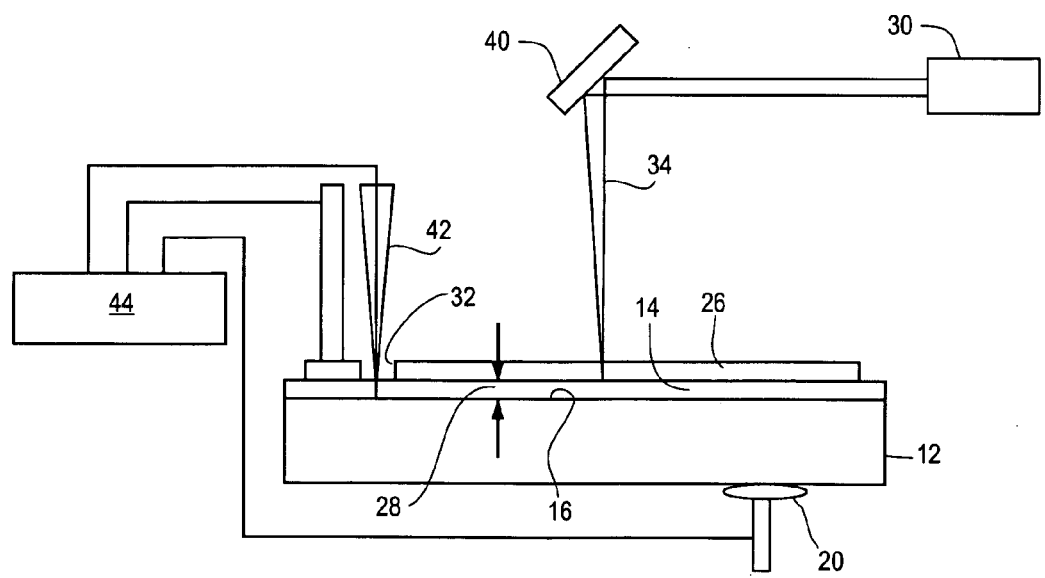
FIG. 5 is an alternative apparatus incorporating the present invention.

The voltage potential applied across the substrate/film interface 16 is provided by a potentiostat 44, such as shown in FIG. 5, electrically connected to the substrate 12 and electrode 26. Advantageously, as a result of the low electrical resistance of the ohmic contact 20 connected to the substrate 12 almost all the applied potential is dropped in the depletion layer. As a result, the voltage applied can be less than 10 volts. Preferably, the voltage potential applied across the substrate/film interface is less than 1 volt.

Referring to FIGS. 1–4, a photon energy source 30, such as a laser, having an emission energy level greater than the voltage potential across the substrate/film interface 16 is directed at the depletion region 18 in the substrate 12. The photon energy source 30 produces a line (or point) 34 of intense light across the width of the substrate. As a result, the electrons (when using a p-type material substrate) arriving at the substrate/film interface 16 is very localized. Preferably, the photon energy source 30 is pulsed, chopped, or modulated to avoid saturation. When the light is off, the potential between the semiconducting substrate 12 and the transparent electrode 26 is reversed so that the molecules move in the opposite direction.

A pivotally mounted mirror 40 pivots to direct the light beam 34 across the substrate/film interface 16. Scanning the light beam 34 across the substrate/film interface 16 causes the molecules to migrate in the same direction of the direction of scan because the location of electrons (when using a p-type material substrate) arriving at the substrate/film interface 16 moves as the light beam 34 moves. Although scanning is preferred, arrays of light beams directed at the depletion region 18 can separate a large number of molecules, such as proteins in a single sweep.

The photon energy source 30 raises the energy level of the substrate 12 at the substrate/film interface 16 above the Fermi level 41 to create electron-hole pairs in the depletion region 18 which are separated by the voltage potential. The separated electrons and holes have opposite charges which cause the electrons to move in a direction opposite of the holes. By proper choice of the substrate 12 (for example, a p-type semiconductor substrate material or n-type semiconductor) and electrode 26 (cathodic or anodic), either electrons or holes can be brought to the substrate/film interface 16 to create a photopotential in the film 14. For example, if a p-type semiconductor substrate material is used, the electrons move toward the substrate/film interface 16.

The magnitude of the photovoltage induced by the photon energy source 30 is proportional to the light intensity and the extent of the band bending. The extent of band bending can be controlled by adjusting the biasing voltage. In one embodiment the bias is kept constant. Preferably, the bias is selected such that the photovoltage is maximized. Most preferably, the applied potential between the substrate 12 and electrode 26 is alternated in such a way that the photopotential is alternated. This causes the analyte molecular motion to alternate between substrate 12 and electrode 26, and thus inhibits the analyte molecules from collecting on either the substrate 12 or electrode 26.

In use, the film 14 containing analyte molecules, i.e. molecules having a charge, is poured onto the substrate 12 through the inlet 32, and fills the gap 28 between the electrode 24 and substrate 12. The voltage potential is applied across the substrate/film interface 16, and the light beam 34 is scanned across the substrate/film interface 16 to create the localized photopotential in the film 14. The analyte molecules disposed in the film 14 react to the photopotential by migrating a distance proportional to the photopotential and the mass of the molecule. Advantageously, an array of photon energy sources can be provided which separate proteins to sequence DNA. The separated analyte molecules can be collected using methods known in the art, such as by using bins or separate microfluidic channels.

While there has been shown and described what are at present considered the preferred embodiments of the invention, it will be obvious to those skilled in the art that various changes and modifications can be made therein without departing from the scope of the invention defined by the appended claims. For example, as shown in FIG. 5, one or more reference electrodes 42 can be used with the embodiment disclosed above to accurately measure the voltage potential drop across the substrate/film interface.

We claim:

1. An apparatus for separating molecules, said apparatus comprising:

a semiconductor material layer;
a counter electrode that is a transparent insulating material having at least one surface coated by a film of a conductive material;
an electrically conductive layer located between and in contact with the semiconductor and in contact with the counter electrode, the electrically conductive layer further including at least two different molecules that are separable by the apparatus;
a voltage source electrically coupled to the semiconductor and the counter electrode wherein the voltage source applies a voltage potential across the electrically conductive layer to thereby generate a depletion region in the semiconductor; and
at least one photon energy source incident upon the semiconductor having the depletion region wherein the photon energy source generates photon energy sufficient to form electron hole pairs that are separated by the voltage potential depletion region thereby generating a photopotential at the surface of the semiconductor material causing charged molecules in the electrically conductive layer in contact with the semiconductor material to move in response to the localized photovoltage, wherein at least one of the photon energy source and the semiconductor is movable relative to the other.

2. The apparatus of claim 1 in which the semiconductor includes a material selected from the group consisting of Si, Ge, GaAs, $TiO_2$, CdS, and ZnO.

3. The apparatus of claim 1, wherein the electrically conductive layer is a film.

4. The apparatus of claim 3, wherein the film comprises an admixture of a composition selected from the group consisting of polyacrylamide, dextran, polymethyl methacrylate and agarose and the at least two different molecules that are being separated by the apparatus.

5. The apparatus of claim 1, wherein the photon energy source produces a focused beam of light to create a localized photopotential at the surface of the semiconductor and located at an interface between the semiconductor and the electrically conductive layer.

6. The apparatus of claim 1, wherein the photon energy source is a laser.

7. The apparatus of claim 1, wherein the photon energy source is a scannable laser.

8. The apparatus of claim 1, wherein the photon energy source is modulated.

9. The apparatus of claim 1 wherein the photon energy source is pulsed.

10. The apparatus of claim 1 wherein the photon energy source is chopped.

11. The apparatus of claim 1, wherein the photon energy source is movable relative to an interface between the semiconductor and the electrically conductive layer to scan photon energy across said interface.

12. The apparatus of claim 1, in which the voltage source is applied between the counter electrode and the semiconductor material using a potentiostat electrically connected to these the counter electrode and to the semiconductor material.

13. The apparatus of claim 1, wherein the voltage source applies a modulated voltage potential.

14. The apparatus of claim 1, wherein said surface is artificially patterned to provide resistance to the molecular motion for separation.

15. The apparatus of claim 1, wherein the voltage source applies an alternating voltage potential.

16. The apparatus of claim 1, wherein the counter electrode is optically tansmissive.

17. The apparatus of claim 1, wherein the counter electrode is indium doped tin oxide.

18. An apparatus for separating molecules, said apparatus comprising:
a semiconductor material layer;
a counter electrode;
an electrically conductive layer located between and in contact with the semiconductor and the counter electrode, the electrically conductive layer further including at least two different molecules that are being separated by the apparatus;
an interface located between the semiconductor material layer and the electrically conductive layer;
a voltage source electrically coupled to the semiconductor and the counter electrode wherein the voltage source applies a voltage potential across the interface to thereby generate a depletion region in the semiconductor; and
at least one photon energy source incident upon the semiconductor having the depletion region wherein the photon energy source generates photon energy sufficient to form electron hole pairs that are separated by the voltage potential depletion region thereby generating a photopotential at the surface of the semiconductor material causing charged molecules in the electrolyte medium in contact with the semiconductor material to move in response to the localized photovoltage, wherein at least one of the photon energy source and the semiconductor is movable relative to the other wherein the counter electrode is a transparent insulating material having at least one surface coated by a film of a conductive material wherein the transparent insulating material is selected from the group of materials consisting of glass and quartz, and the conductive material is selected from the group of materials consisting of gold and platinum.

19. A method for separating molecules, said method comprising:
applying a voltage between a semiconductor material and a counter electrode to generate voltage potential that creates a depletion region in the semiconductor material, wherein the semiconductor material and the counter electrode are separated by a gap that contains an electrically conductive layer that is in contact with the semiconductor material and with the counter electrode, wherein the electrically conductive layer contains an admixture of a plurality of different charged analyte molecules of interest;
irradiating a location on the semiconductor material layer that corresponds to the depletion region with a photon energy source, wherein the photon energy source has sufficient energy to form electron hole pairs in the depletion region wherein the electron hole pairs are separated by the voltage potential to form a localized photopotential; and
moving the location on the semiconductor material layer that is irradiated by the photon energy source to create a corresponding change in photopotential at the interface of the semiconductor material and the electrically conductive layer thereby inducing the migration of the charged analyte molecules wherein at least two of the plurality of different charged analyte molecules migrate at different rates to effectuate molecular separation.

20. The method of claim 19 in which the semiconductor material is selected from the group consisting of Si, Ge, GaAs, $TiO_2$, CdS, and ZnO.

21. The method of claim 19, wherein the electrically conductive layer is a film.

22. The method of claim 19 wherein at least two of the plurality of different analyte molecules are separated from the admixture of a plurality of different analyte molecules.

23. The method of claim 19 wherein the electrically conductive layer is a film that resists movement of analyte molecules to facilitate separation of different analyte molecules.

24. The method of claim 19 wherein the applied voltage potential is alternated to cause the motion of the charged analyte molecules to alternate between the semiconductor material and the counter electrode.

25. The method of claim 19, including focusing the photon energy to produce a beam of light to create a localized photopotential at the surface of the semiconductor material photosensitive and located at the interface between the semiconductor material and the electrically conductive layer.

26. The method of claim 19, wherein the photon energy source is a laser.

27. The method of claim 19, wherein the photon energy source is applied intermittently.

28. The method of claim 27 wherein a reversing potential is applied between the semiconductor material and the counter electrode when the photon energy source is in a light off cycle.

29. The method of claim 19 including moving the photon energy source relative to an interface between the semiconductor and the electrically conductive layer to scan photon energy across said interface.

30. The method of claim 19 wherein the photon energy source is an array of light beams.

31. A method for separating molecules, said method comprising:

applying a voltage between a semiconductor material and a counter electrode to generate voltage potential that creates a depletion region in the semiconductor material, wherein the semiconductor material and the counter electrode are separated by a gap that contains an electrically conductive layer that is in contact with the semiconductor material and with the counter electrode, wherein the electrically conductive layer contains an admixture of a plurality of different charged analyte molecules of interest;

irradiating a location on the semiconductor material layer that corresponds to the depletion region with a photon energy source, wherein the photon energy source has sufficient energy to form electron hole pairs in the depletion region wherein the electron hole pairs are separated by the voltage potential to form a localized photopotential; and moving the location on the semiconductor material layer that is irradiated by the photon energy source to create a corresponding change in photopotential at the interface of the semiconductor material and the electrically conductive layer thereby inducing the migration of the charged analyte molecules wherein the electrically conductive layer is a film and wherein the film comprises an admixture of a composition selected from the group consisting of polyacrylamide, dextran, polymethyl methacrylate and agarose and the at least two different molecules that are being separated by the apparatus.

* * * * *